US008337459B1

(12) United States Patent
Taylor et al.

(10) Patent No.: US 8,337,459 B1
(45) Date of Patent: Dec. 25, 2012

(54) DEVICE AND METHOD TO MONITOR CARBOHYDRATE LOADS FOR DIABETICS USING A BAR CODE SCANNER AND DOSING INSULIN

(76) Inventors: Michael Taylor, Jacksonville, FL (US); James Taylor, Jacksonville, FL (US)

( * ) Notice: Subject to any disclaimer, the term of this patent is extended or adjusted under 35 U.S.C. 154(b) by 0 days.

(21) Appl. No.: 13/070,771

(22) Filed: Mar. 24, 2011

(51) Int. Cl.
*A61M 1/00* (2006.01)
(52) U.S. Cl. ........................................ 604/151
(58) Field of Classification Search .................. 604/151
See application file for complete search history.

(56) References Cited

U.S. PATENT DOCUMENTS

| | | | | |
|---|---|---|---|---|
| 5,819,735 | A | * | 10/1998 | Mansfield et al. ............ 600/300 |
| 2003/0007996 | A1 | | 1/2003 | Graham et al. |
| 2003/0106940 | A1 | * | 6/2003 | Bukowski ................. 235/462.45 |
| 2003/0208113 | A1 | * | 11/2003 | Mault et al. .................... 600/316 |
| 2005/0197553 | A1 | | 9/2005 | Cooper |
| 2007/0078818 | A1 | | 4/2007 | Zivitz et al. |
| 2008/0033827 | A1 | | 2/2008 | Kuang et al. |
| 2009/0275002 | A1 | | 11/2009 | Hoggle |
| 2009/0297448 | A1 | | 12/2009 | Yan et al. |
| 2010/0049164 | A1 | | 2/2010 | Estes |
| 2010/0280918 | A1 | * | 11/2010 | Balent ............................. 705/26 |

* cited by examiner

*Primary Examiner* — Nicholas Lucchesi
*Assistant Examiner* — Jason Flick
(74) *Attorney, Agent, or Firm* — Thomas C. Saitta

(57) ABSTRACT

In order for diabetics to maintain appropriate blood sugar levels, this application will enable a person to determine the amount of carbohydrates in a particular food item in any restaurant. With the modern technology of applications for smart phones or hand held computer devices that can read barcodes, the information can easily be retrieved for appropriate use. Software can be integrated between the hand held computer device that will enable an insulin pump to automatically and accurately dose the appropriate amount of insulin that is required.

11 Claims, 2 Drawing Sheets

DEVICE AND METHOD TO MONITOR CARBOHYDRATE LOADS FOR DIABETICS USING A BAR CODE SCANNER AND DOSING INSULIN

BACKGROUND OF THE INVENTION

A. Field of the Invention

This relates to enabling an individual to properly calculate carbohydrate loads from restaurant menus. This is particularly important for diabetics to properly monitor insulin levels.

B. Prior Art

There are many prior art references that teach devices and provide information related to nutrition. A representative example of this type of patent can be found in the prior art is Hoggle, U.S. Publication 2009/0275002. This application and method is provided for the user to determine individual nutritional information and requirements pertaining to menus and recipes that suited to an individual user. In this application, an individual uses a barcode scanner to scan information regarding a menu and altar the intake depending on information that is received. The Hoggle reference does not specifically relate to diabetic compliance, but it provides information to integrate information that would be helpful for a diabetic.

Another patent publication that deals specifically with diabetes is Graham, U.S. Publication 2002/007996. The Graham discusses a method for diet planning, labeling, and promotion of decaffeinated coffee. Again, this deals only with one item.

Another example in the prior art is Kuang, which is specifically related to diet control and allows an individual to input information and store the information about foods, providing warnings concerning consumption of foods. Again, this is not specifically related to diabetes and is not integrated with the insulin pump.

Some of the other prior art also deals with proper or appropriate insulin dosing found on the insulin pump. An example of this is Zivitz. However, this is not an automatic system, and an individual must first calibrate the amount of insulin on the pump.

As was discussed earlier, this device will allow an individual to use a barcode scanner to scan items on a restaurant menu to specifically determine the carbohydrate load, which is important if not vital to a diabetic. This information can then be tailored and integrated specifically to the insulin pump so that the appropriate amount of insulin is injected.

With this device the exact amount of insulin that needs to be dosed can be calculated for individuals who need to inject and do not use a pump.

This device and method eliminates guesswork therefore resulting in a greater quality of life for the diabetic patient and cost savings by not dosing too much insulin.

BRIEF SUMMARY OF THE INVENTION

It is very important for diabetics to monitor carbohydrate loads. Carbohydrates quickly turn into sugar and, for a diabetic whose body has difficulty processing sugars, this can be a problematic.

It is imperative for a diabetic patient or persons suffering from diabetes to insure that he or she receives the appropriate insulin dosage so that the carbohydrate, which is present in all foods and quickly turns into sugar when eaten, is properly processed. Diabetics do not produce enough insulin by themselves to sufficiently break down sugar. Insulin breaks down the sugar and allows a healthy lifestyle.

In order to properly maintain appropriate sugar levels during the day, the diabetic is checking his or her blood sugar levels throughout the day.

There are also insulin devices, including insulin pumps that automatically provide the appropriate amount of insulin or insulin can be taken in injectable form or a pill form.

In the usual case, an individual will set the insulin pump to the appropriate dose depending on an educated guess, and then when the person eats, he or she then administers the estimated amount of insulin that is required. However, there is guess work, depending on whether or not an individual knows exactly how much insulin to dose. This is particularly true in a restaurant setting where the exact carbohydrate load is unknown.

For diabetics eating in restaurants, it is impossible to determine the carbohydrate load of certain foods because each restaurant prepares the food differently, and although there are some probable ranges of carbohydrate loads for certain food groups, it may vary from restaurant to restaurant.

In this application, the restaurant places a barcode next to a particular food item. The individual then scans the barcode that would tell him or her, among other things, the carbohydrate load of the particular food.

In one embodiment the information about the carbohydrate load can then be transmitted from the barcode reader to an insulin pump, and the information from the pump can be integrated so that the appropriate insulin dose can be programmed into the pump and administered to the individual prior to eating a particular food. This would eliminate the guess work.

In an alternative embodiment, the person would scan the barcode using the barcode reader and this would indicate the amount of carbohydrates that will be ingested. Using this information, the person can then determine the appropriate amount of insulin to inject prior to eating.

If a diabetic patient does not dose the appropriate amount, it may affect the health of the individual. If too much insulin is administered, an individual's blood sugar may become too low, and if not enough insulin is administered, the blood sugar may go too high.

This application can also be used by individuals who do not use insulin pumps but who find it necessary to calculate the required amount of insulin that must be injected in order to maintain appropriate blood sugar levels.

The individual will use a specific barcode reader or diabetic food scanner to scan the restaurant's barcodes to determine the appropriate carbohydrate load. The data would then be transmitted from the food scanner to the insulin pump to dose the appropriate amount of insulin.

Additionally, the initial information concerning the carbohydrate loads would be posted or displayed on the food scanner to indicate how many units of insulin to dose if the individual is not using a pump. If the person knows the exact amount of insulin, the person needs to only inject himself one time and not multiple times.

DETAILED DESCRIPTION OF THE EMBODIMENTS

Figure 1:
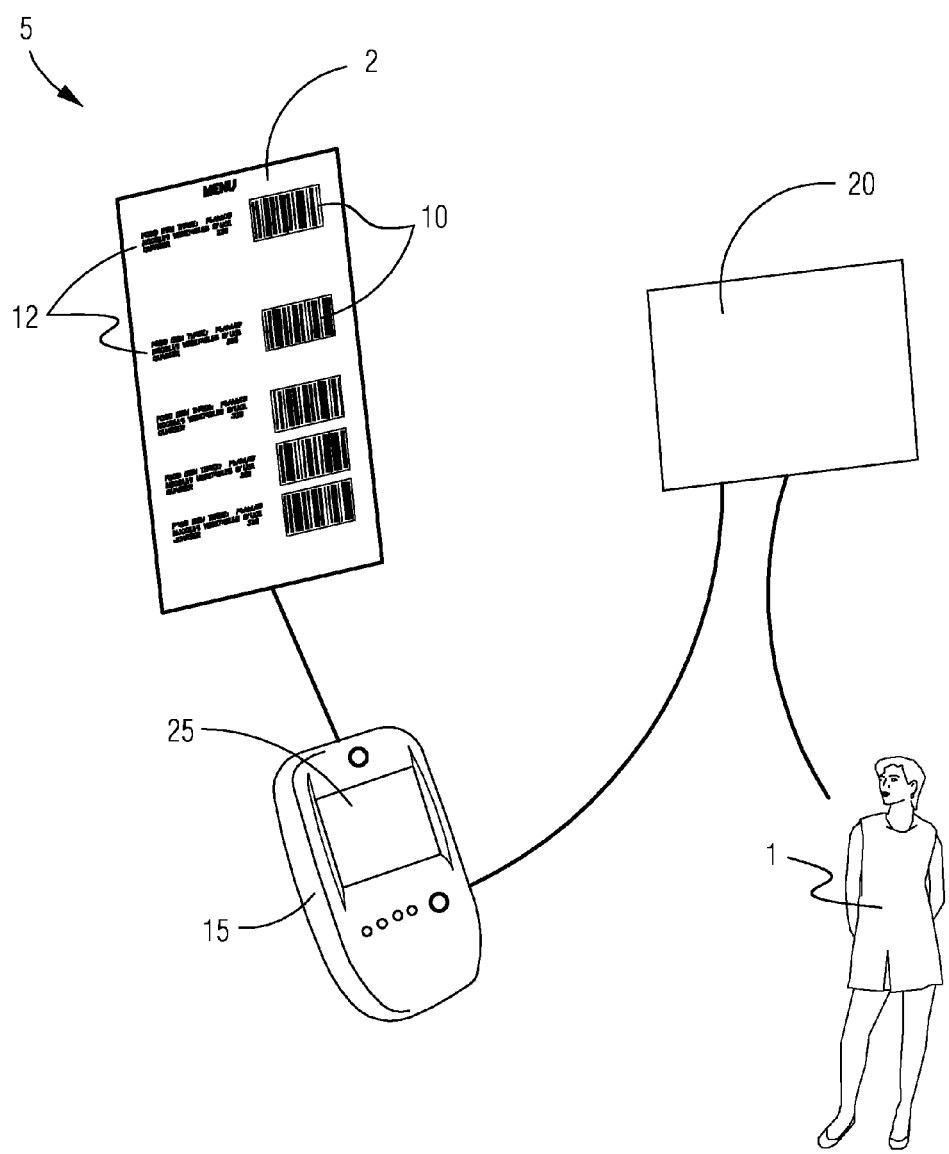
FIG. 1 is a depiction of the device's components.
Figure 2:
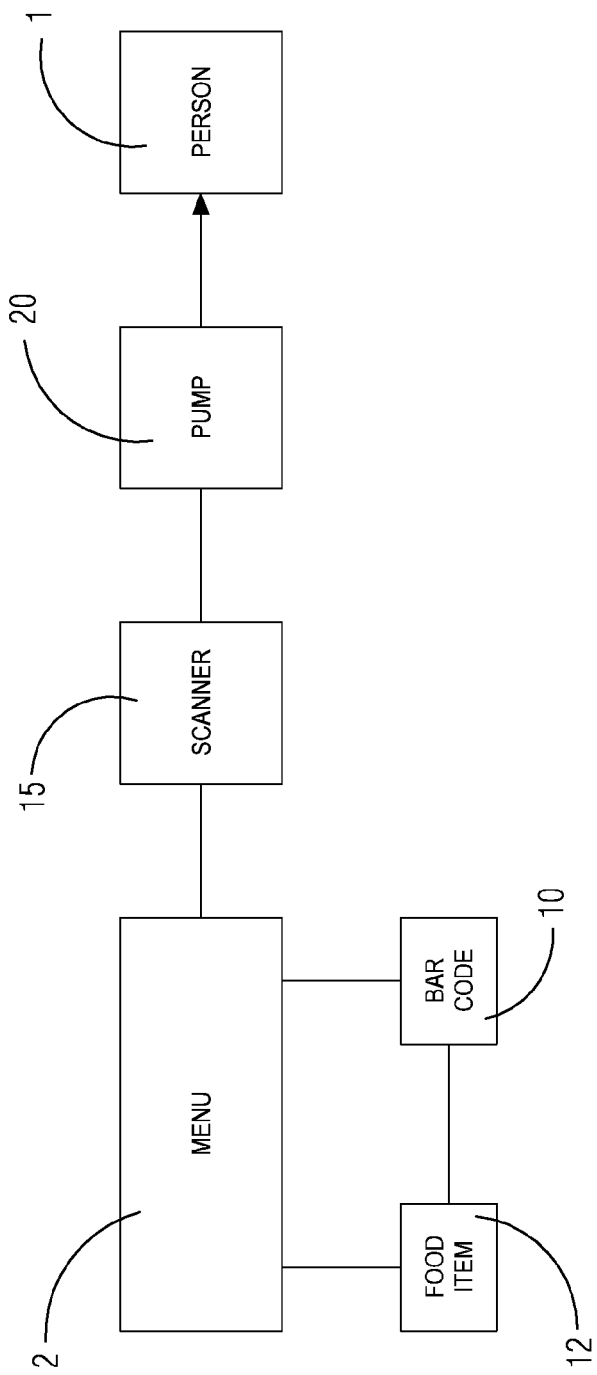
FIG. 2 is a schematic of the components of the device.

This is a method 5 by which an individual 1 can appropriately determine the amount of insulin to be administered through a pump or other injectable device to maintain an appropriate blood sugar level. This is particularly true of diabetic patients who could suffer adverse health consequences by not appropriately monitoring their diet.

As carbohydrates are ingested, the diabetic person does not have enough insulin to break down the sugar that is produced as the carbohydrates are digested. If the blood sugar level is too high damage to organs may occur and if the blood sugar is too low, the person may become dizzy and faint.

Unfortunately, the damage from diabetes is permanent so it is imperative to properly monitor the appropriate blood sugar levels at all times.

In this application, a barcode reader 15 or diabetic food scanner, which is a handheld device scans or reads a barcode 10 that has been placed on the restaurant menu 2 in close proximity to the food item 12 or on a separate sheet provided by the restaurant.

Regardless of where the barcode is placed, separate barcodes 10 would be placed beside each food item 12 on the menu 2. In the barcode, information about the amount of carbohydrates would be embedded; other nutritional information may also be included in the barcode but this application specifically deals with the amount of carbohydrates in a particular food item. After an individual scans the barcode on the menu, the information about the carbohydrates that are contained in the food are displayed 25 for the individual 1 on the handheld device 15.

Because each restaurant is different, different carbohydrate loads may be found from restaurant to restaurant. It is the carbohydrate load that determines the amount of insulin that is needed because the carbohydrate turns into sugar, which must be monitored by the diabetic patient. This application would eliminate the guess work.

Software will provide a means to communicate between the handheld device and the insulin pump 20 will be provided to insure that the appropriate amount of insulin is being dosed through the pump 20. This software will enable wireless communication between the barcode reader and the insulin pump 20 to properly dose the required amount of insulin to the person 1.

In an alternative embodiment the information would be displayed on the barcode reader so an individual may determine the appropriate amount of insulin to be administered if the person does not have a pump and needs to inject an appropriate amount of insulin prior to eating.

While the embodiments of the invention have been disclosed, certain modifications may be made by those skilled in the art to modify the invention without departing from the spirit of the invention.

The inventors claim:

1. A method to monitor carbohydrate loads for diabetics using a bar code reader comprising the steps of:
   (a) ascertaining the actual carbohydrate load of an individual food item as served in a particular restaurant;
   (b) associating said actual carbohydrate load with a particular bar code as stored information;
   (c) placing a description of said individual food item on a printed sheet;
   (d) placing said bar code on said printed sheet in close proximity to said description of said individual food item;
   (e) providing said printed sheet to an individual dining in said particular restaurant;
   (f) scanning said particular bar code with a bar code reader device to extract said stored information;
   (g) calculating a correct amount of insulin to be delivered based on said stored information; and
   (h) providing said calculated correct amount of insulin to said individual.

2. The method of claim 1, further comprising the step of providing said stored information to said individual.

3. The method of claim 1, wherein said step of providing said calculated correct amount of insulin to said individual comprises displaying said calculated correct amount of insulin on said bar code reader device.

4. The method of claim 2, wherein said step of providing said stored information to said individual comprises displaying said stored information on said bar code reader device.

5. The method of claim 4, wherein said step of providing said calculated correct amount of insulin to said individual comprises displaying said calculated correct amount of insulin on said bar code reader device.

6. The method of claim 1, wherein said step of providing said calculated amount of insulin to said individual comprises delivering said calculated amount of insulin to an insulin pump, and further comprising the step of:
   (i) delivering insulin from said insulin pump to said individual.

7. The method of claim 6, wherein said step of delivering said calculated amount of insulin to an insulin pump is performed with wireless communication.

8. The method of claim 1, wherein said step of placing said bar code on said printed sheet in close proximity to said description of said individual food item comprises placing said bar code on a menu.

9. The method of claim 1, further comprising the step of repeating said method steps (a) through (h) for different individual food items.

10. The method of claim 6, further comprising the step of repeating said method steps (a) through (i) for different individual food items.

11. The method of claim 6, wherein said insulin pump is programmable, and further comprising the step of:
    (j) providing software integrated between said bar code reader device and said insulin pump whereby said software properly doses said insulin to said individual.

* * * * *